United States Patent [19]
Working, III

[11] Patent Number: 6,071,175
[45] Date of Patent: Jun. 6, 2000

[54] NATAL SUPPORT

[75] Inventor: Loren F. Working, III, Wadsworth, Ohio

[73] Assignee: CMO, Inc., Barberton, Ohio

[21] Appl. No.: 09/193,082

[22] Filed: Nov. 16, 1998

[51] Int. Cl.$^7$ .................................................. A41D 13/04
[52] U.S. Cl. ...................... 450/155; 2/44; 2/45; 128/90.1
[58] Field of Search ...................... 2/44.45, 92; 450/155, 450/135, 136, 137, 140, 149; 128/90.1, 100.1, 101, 99.1

[56] References Cited

U.S. PATENT DOCUMENTS

| | | | |
|---|---|---|---|
| 184,153 | 11/1876 | Holton | 450/155 |
| 1,469,069 | 9/1923 | Freedenberg | 450/155 |
| 2,282,021 | 5/1942 | Benningfield | 128/100.1 |
| 3,605,731 | 9/1971 | Tigges | 128/100.1 |
| 3,931,816 | 1/1976 | Waldmann | 128/100.1 |
| 4,195,640 | 4/1980 | Castiglia | 128/100.1 |
| 5,217,403 | 6/1993 | Nobbs . | |
| 5,241,704 | 9/1993 | Sydor | 2/44 |

*Primary Examiner*—Gloria M. Hale
*Attorney, Agent, or Firm*—Sand & Sebolt

[57] ABSTRACT

A device for providing natal support and alleviating pain in a pregnant woman includes a support member, an apron, and a strap, with the strap removably attached to the apron. The strap may be removed after installation and adjustment of the natal support on the pregnant woman. The natal support alleviates pain by providing support to the lower abdomen and distributing the weight of the fetus and enlarged uterus over a large portion of the lower back. Additionally, the strap facilitates installation and proper positioning of the natal support on the human body by holding the apron in place on the back while it is being adjusted.

15 Claims, 6 Drawing Sheets

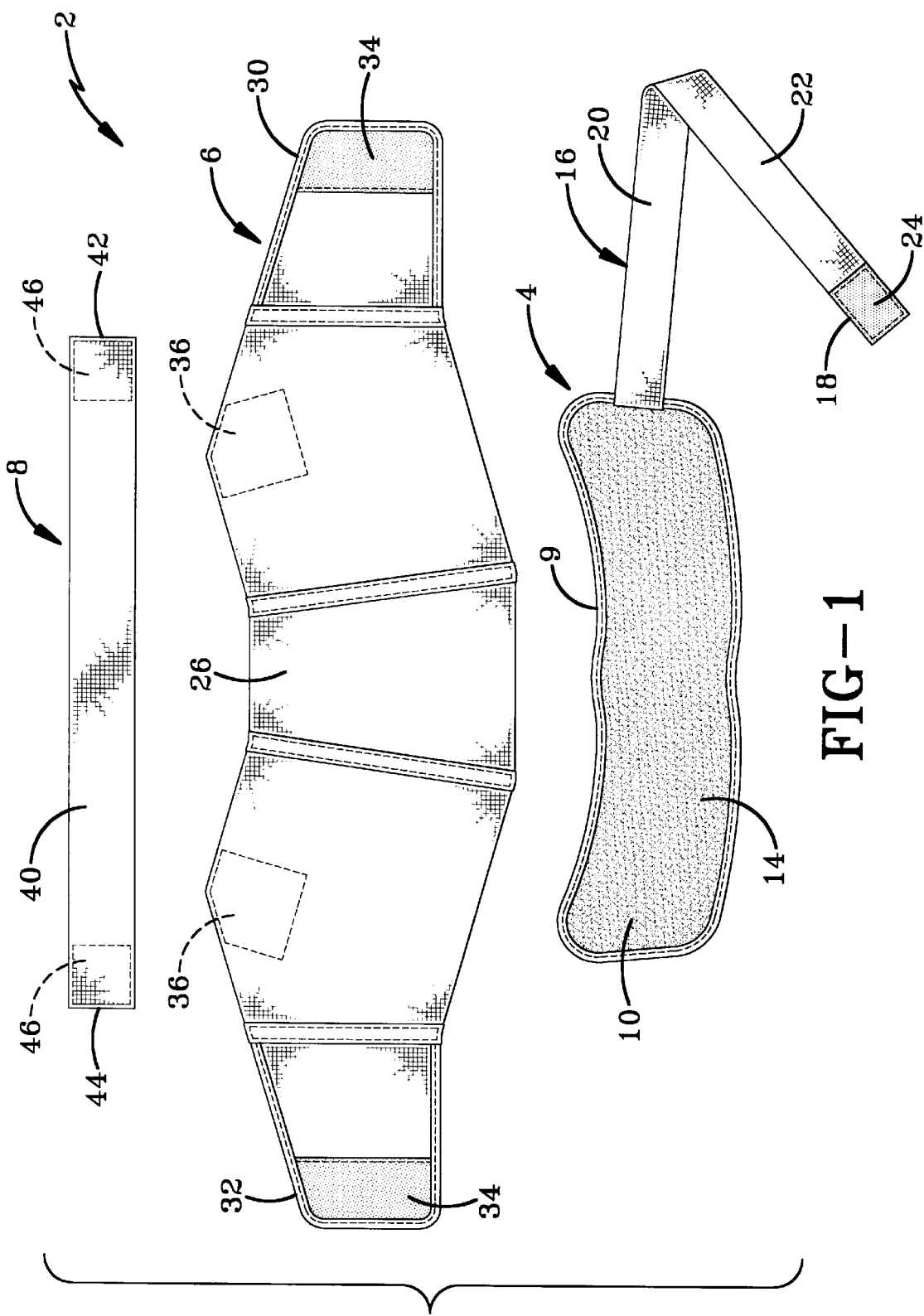

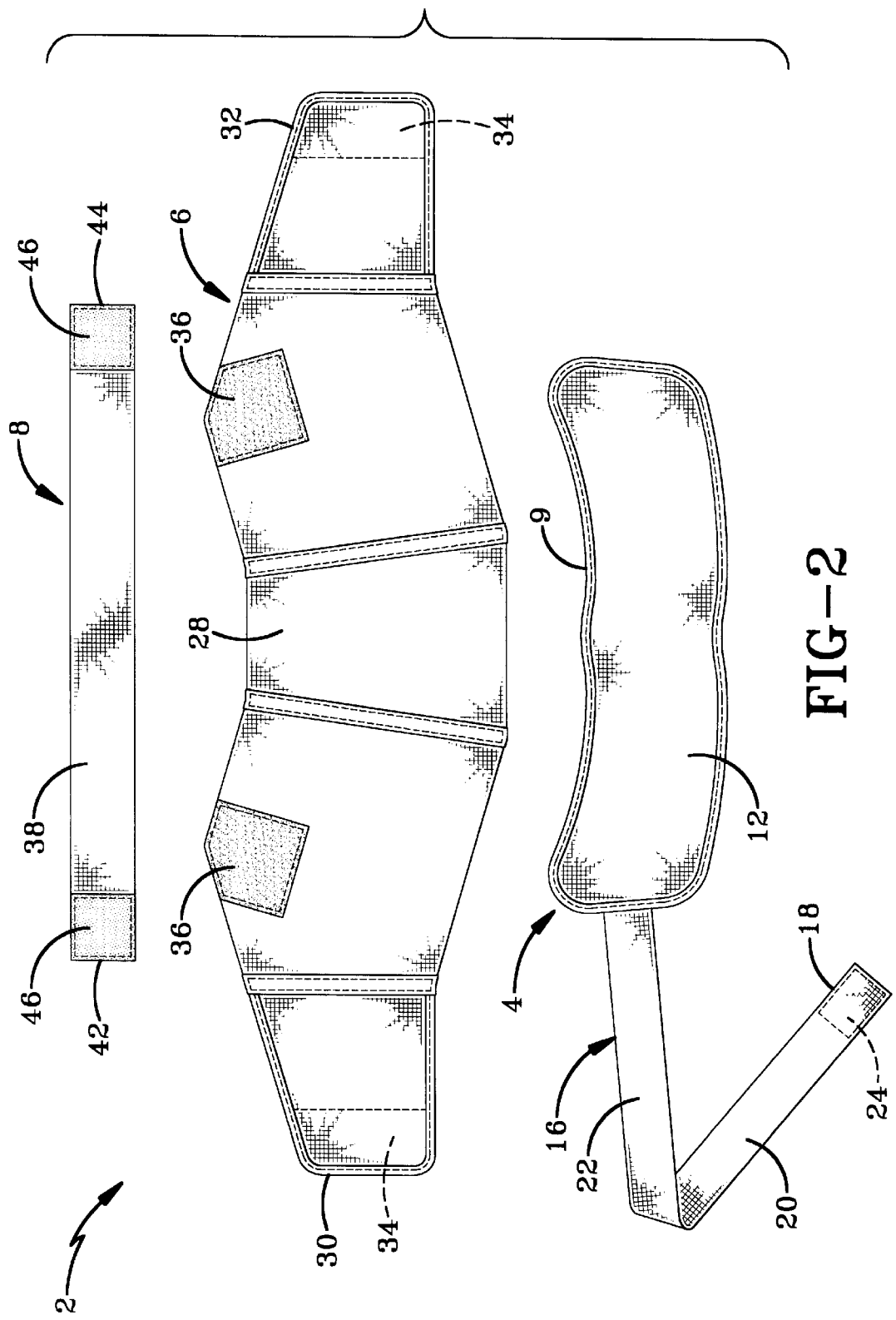

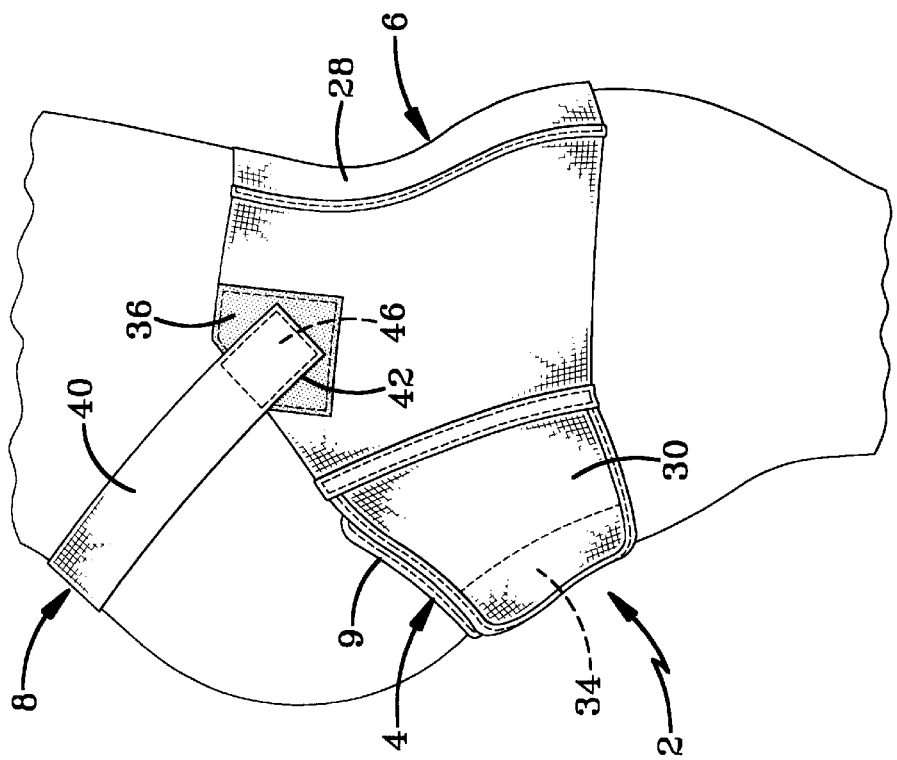
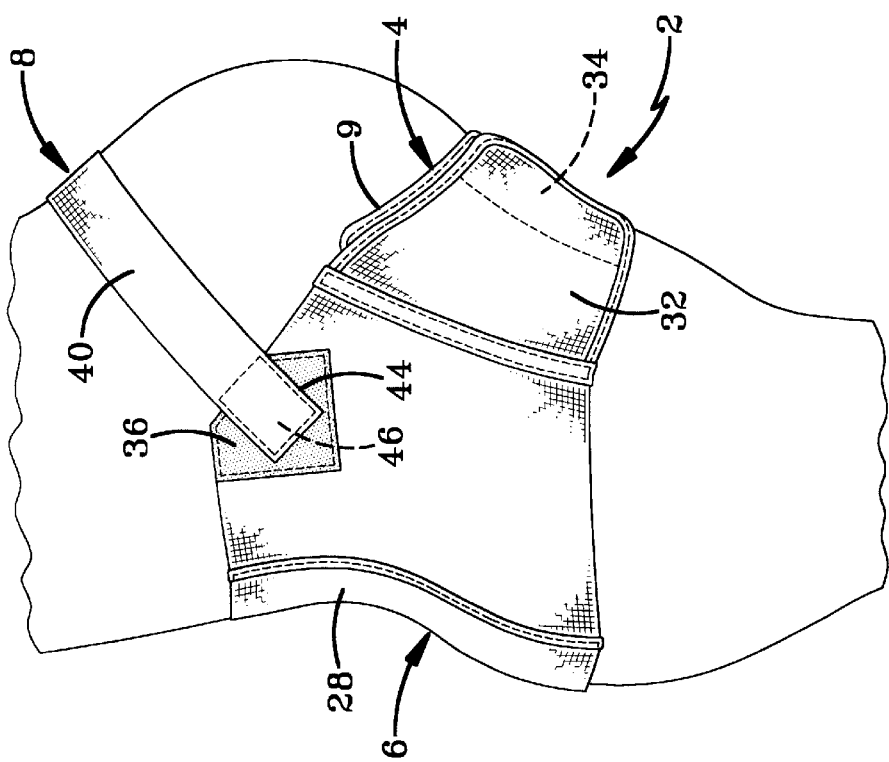

NATAL SUPPORT

BACKGROUND OF THE INVENTION

1. Technical Field

This invention generally relates to a support for the human body, and more particularly to a device that provides abdominal and back support to a pregnant woman. Specifically, the invention relates to a natal support having an auxiliary strap to facilitate installation and positioning of the support.

2. Background Information

The human spine is a complex assembly of bones, ligaments, and muscles. The construction of the human spine provides support sufficient to allow the human being to carry heavy loads, yet additionally provides sufficient flexibility for bending over to tie the shoe laces.

The weight of a fetus and the enlarged uterus of a pregnant woman results in a significant force applied to the spine. Such force results in forward deflection of the spine and resultant muscle strain and pain. Inasmuch as this pain results primarily from deflection of the spine, a support that restores the spine to its natural undeflected condition would, concomitantly, tend to alleviate much of the pain caused by such deflection.

While many such devices have been attempted, the most successful devices have utilized a support member in the front of the body that extends across the lower abdomen and underneath the uterus. This support member is attached to an apron extending around the lower back which urges the support member rearward, thus tending to counteract the forward deflection of the lower spine caused by the weight of the fetus.

Such devices are not, however, without limitations. Such support devices, to be effective, must utilize tensile forces to urge the support member rearward. Installation of the support devices with sufficient tensile forces to be effective is difficult due to the magnitude of the forces required and the awkward positioning of the supports. Moreover, such supports can be difficult to install properly due to the awkwardness resulting from the enlarged physique of the pregnant woman. Additionally, such supports may require periodic incremental adjustment which may be difficult to perform easily. Also, such devices must be comfortable to the wearer and not unduly limit movement.

One such device has used a support member and an apron, with the apron additionally containing a strap affixed at one end to the apron and having a hook-and-loop attachment at the other end with the apron. While this particular device is effective for its intended use, the device is not without limitations. The fixed attachment of the strap to the apron prevents the strap from being completely removed from the apron. The fixed attachment of the strap provides only limited adjustment thereby limiting the utility of the device. An improved device would allow the strap to be adjustable at both ends or removable from the device.

Thus, the need exists for a natal support which is easy to install and adjust, is comfortable to wear for extended periods of time, and is relatively easy to remove and clean.

SUMMARY OF THE INVENTION

In view of the foregoing, an objective of the invention includes providing a natal support that is easy to install.

An additional objective of the invention is to provide a natal support that is comfortable to wear.

Another objective of the invention is to provide a natal support that alleviates the back pain experienced by women during pregnancy.

Another objective of the invention is to provide a natal support that supports the abdomen during pregnancy.

Another objective of the invention is to provide a natal support that is easy to remove.

Another objective of the invention is to provide a natal support that can be worn for long periods of time.

Another objective of the invention is to provide a natal support that can be adjusted easily.

Another objective of the invention is to provide a natal support that can be washed or cleaned easily.

Another objective of the invention is to provide a natal support that allows the weight of the fetus and the enlarged uterus to be supported by a large portion of the spine.

Another objective of the invention is to provide a natal support that applies a force to the lower abdomen.

These and other objectives and advantages of the invention are obtained from the natal support, the general nature of which can be stated as including a support member, an apron having a first flap and a second flap, the first and second flaps being attached to the support member, a strap having a first end and a second end, and the first and second ends being removably attached to the apron.

BRIEF DESCRIPTION OF THE DRAWINGS

The preferred embodiment of the invention, illustrative of the best mode in which applicant has contemplated applying the principles of the invention, is set forth in the following description and is shown in the drawings and is particularly and distinctly pointed out and set forth in the appended claims.

FIG. 1 is an exploded view of the natal support of the present invention showing one side of the components thereof;

FIG. 2 is an exploded view of the natal support of the present invention showing another side of the components thereof;

FIG. 8 is a left side perspective view of the support member, apron, and strap of the present invention installed on a human;

FIG. 9 is a right side perspective view of the support member, apron, and strap of the present invention installed on a human.

Similar numbers refer to similar parts throughout the specification.

DESCRIPTION OF THE PREFERRED EMBODIMENTS

Figure 4:
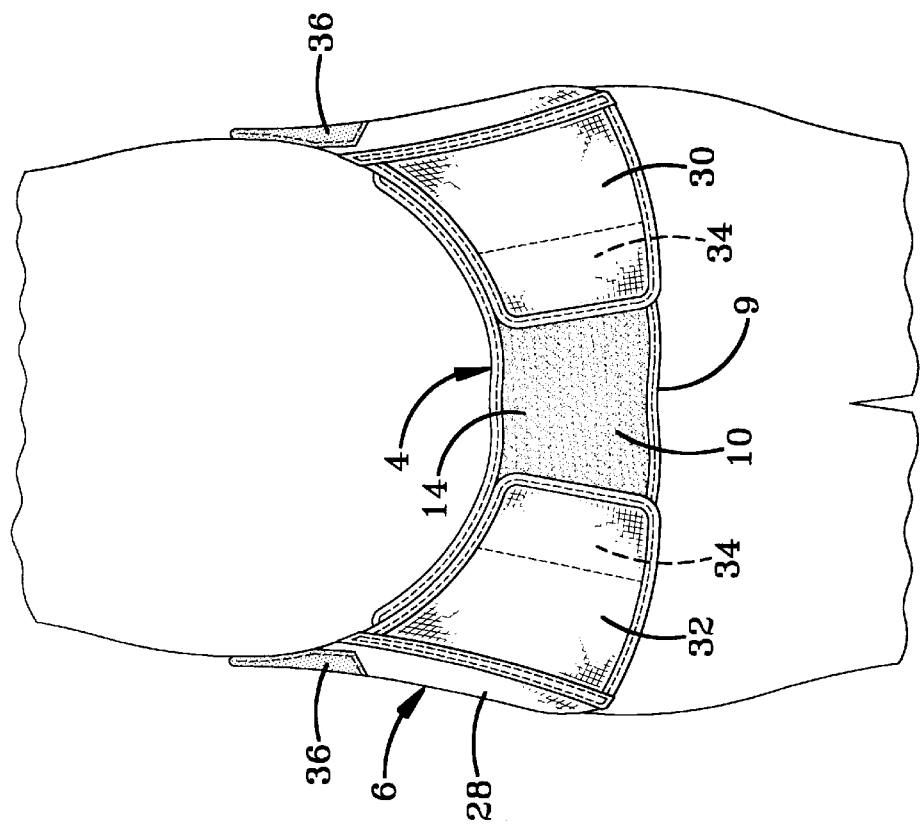
FIG. 4 is a front perspective view of the support member and the apron of the present invention installed on a human.
Figure 3:
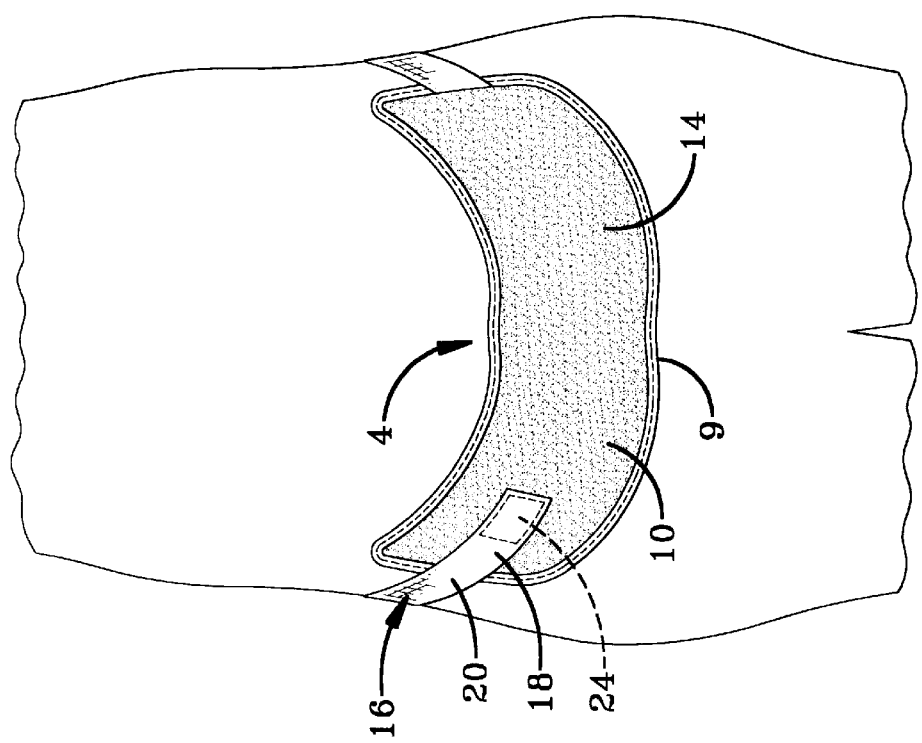
FIG. 3 is a front perspective view of the support member of the present invention installed on a human.

The natal support of the present invention is indicated generally by the numeral 2 in the accompanying drawings. Natal support 2 includes a support member 4, an apron 6, and a strap 8. Support member 4 and strap 8 cooperate with apron 6 to provide abdominal support and alleviate back pain in a pregnant woman.

Support member 4 includes a support body 9 having a first face 10 and a second face 12 opposed thereto. First face 10 contains a plurality of loops 14 that cooperate with hooks 24 to form hook-and-loop fasteners having complemental parts which adhere to each other when pressed together and are adapted for use as a closure fastener. Support body 9 is manufactured of an appropriate fabric having flexibility, body, and non-elasticity, although departure from these properties is possible without departing from the spirit of the present invention.

Support body 9 is preferably of the shape depicted in FIGS. 1–2, although other shapes may be utilized without departing from the spirit of the present invention. FIGS. 1–2 show that the periphery of support body 9 is variously curved (an upper concave face with a lower convex face), and the edges of support body 9 are preferably rounded. The various curves and rounded edges of support body 9 are intended to enhance fit and comfort of natal support to, thereby enhancing the likelihood of its use.

Support member 4 additionally includes a belt 16 having one end sewn to support body 9 and having a terminal end 18, a first surface 20, and a second surface 22. As can be seen in FIGS. 1–2, first surface 20 of belt 16 faces the same direction as first face 10 of support body 9, and second surface 22 faces the same direction as second face 12. Terminal end 18 additionally carries hooks 24 on second surface 22 which, as indicated above, cooperate with loops 14 to constitute hook-and-loop fasteners. Belt 16 is manufactured of an appropriate flexible material such as an elastic nylon webbing, although departure from these properties is possible without departing from the spirit of the present invention.

Apron 6 is a flat body of relatively thin fabric such as elasticized cotton. Apron 6 can be constructed of a wide variety of materials, and can be either elastic or inelastic in character without departing from the spirt of the present invention. Apron 6 is preferably of a shape like that depicted in FIGS. 1 and 2 having a concave upper edge and a convex lower edge. Other shapes may, however, be utilized without departing from the spirit of the present invention.

Figure 6:
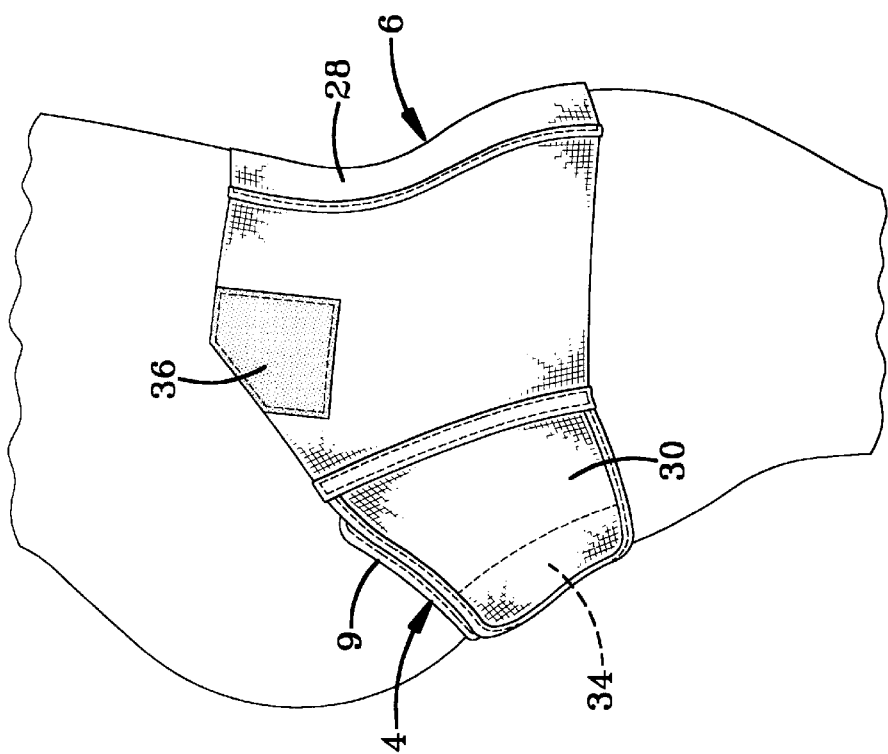
FIG. 6 is a right side perspective view of the support member and the apron of the present invention installed on a human.
Figure 5:
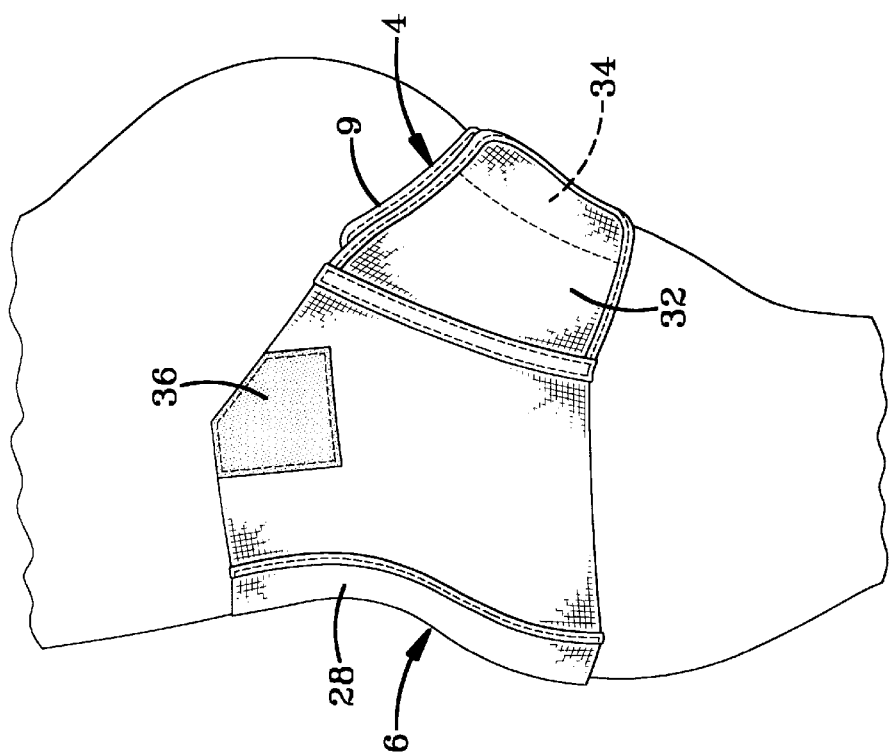
FIG. 5 is a left side perspective view of the support member and the apron of the present invention installed on a human.
Figure 7:
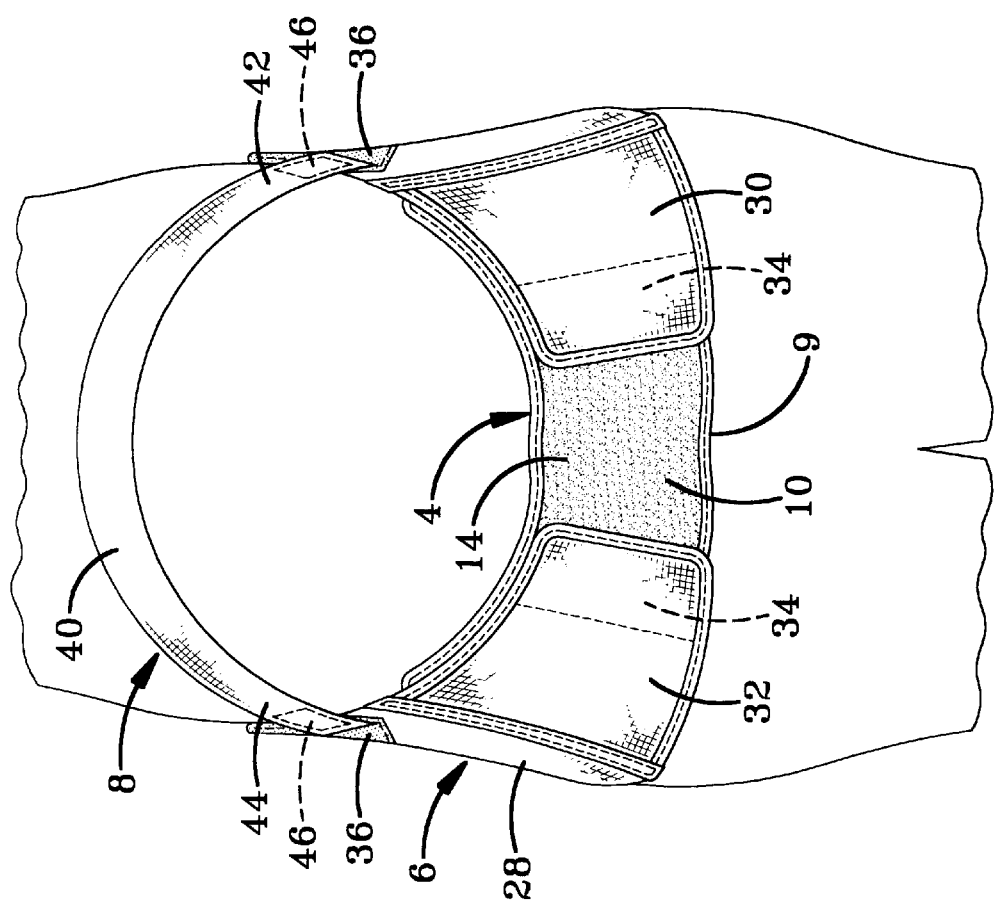
FIG. 7 is a front perspective view of the support member, apron, and strap of the present invention installed on a human.

Apron 6 contains an internal surface 26 and an external surface 28 it opposed thereto, as well as a first flap 30 and a second flap 32 at alternate ends thereof. First and second flaps 30 and 32 contain hooks 34 on internal surface 26. Hooks 34 are similar in function to hooks 24. As can be seen in FIGS. 4–9, hooks 34 cooperate with loops 14 of support body 9 when support 2 is worn by a woman.

Apron 6 additionally contains a pair of looped areas 36 on external surface 28. Each looped area 36 includes a plurality of loops that function similar to loops 14. As is shown in FIG. 2, looped areas 36 lie between first and second flaps 30 and 32. Moreover, as is shown in FIGS. 5–6 and FIGS. 8–9, looped areas 36 are spaced from each other so that when apron 6 is installed on a human body, looped areas 36 lie approximately at the sides of the human.

As can be seen in FIGS. 1–2, apron 6 is, in the preferred embodiments, constructed of a plurality of panels sewn together to facilitate a close fit on the body of the pregnant woman. Each panel is connected to another panel by a hinge member that promotes the fit of support 2 on the human body. In the preferred embodiment of the invention, four hinge members are used to hold five panels together. The edges of apron 6 are preferably rounded. Both the construction of apron 6 and the rounded aspect to its edges are intended to enhance the fit and comfort of apron 6 on the body, thereby encouraging its use. Other construction methods, may, of course, be employed without departing from the spirit of the present invention.

In accordance with one of the main features of the invention, strap 8 is a flat body of flexible fabric such as an elastic nylon webbing, although other materials, elastic and inelastic, may be used without departing from the spirit of the present invention. Strap 8 includes an inner surface 38 and an outer surface 40 opposed thereto, as well as a first end 42 and a second end 44 at alternate ends thereof. First and second ends 42 and 44 contain a plurality of hooks 46 on inner surface 38. Hooks 46 operate similarly to hooks 24, and are intended to cooperate with looped areas 36.

Natal support 2 is installed on the human body by first positioning second face 12 of support body 9 against the lower abdomen. Belt 16 is then wrapped circumferentially around the lower back and hooks 24 are engaged with loops 14 such that support member 4 is held in position on the human body.

Apron 6 is then installed on the lower back. In accordance with the objectives of the present invention, apron 6 may be installed on the back with or without the assistance of strap 8. Apron 6 is positioned on the lower back such that internal surface 26 lies against the back, and first and second flaps 30 and 32 are engaged with loops 14. If desired, strap 8 can be installed such that inner surface 38 rests against the body and hooks 46 of first and second ends 42 and 44 cooperate with looped areas 36. First and second flaps 30 and 32 can then be adjusted by detachment and reattachment with loops 14 until the correct fit is achieved. Strap 8 serves to facilitate the correct installation of apron 6 on the back because strap 8 holds apron 6 in position while first and second flaps 30 and 32 are adjusted with respect to support body 9.

As mentioned hereinbefore, proper fit of natal support 2 is achieved when the installed components assert a compressive force on the body. As such, first and second flaps 30 and 32 must be in tension with respect to support body 9. Thus, detachment of hooks 34 of either first flap 30 or second flap 32 from loops 14 may result in significant movement of apron 6 due to its elastic character. In accordance with the objectives of the present invention, strap 8 serves to prevent such movement and to keep apron 6 in place while first and second flaps 30 and 32 are adjusted with respect to support body 9.

When the proper fit is achieved between apron 6 and support body 9, strap 8 may be removed if desired. If left in place, strap 8 serves to retain support member 4 and apron 6 in position on the human body.

When support member 4 and apron 6 are fully installed on the human body, the tensile force of apron 6 urges support member 4 against the lower abdomen. Such compressive force tends to straighten the spine and counteract the deflection of the spine caused by the weight of the fetus and the enlarged uterus. Additionally, as is indicated in FIGS. 5–6 and 8–9, and in accordance with the objectives of the present invention, the compressive force applied to the lower abdomen is distributed over a relatively large area of the back. It is preferred that apron 6 extend from the lower rib cage to the upper pelvis. As such, the weight of the fetus and the enlarged uterus is, in effect, distributed over a large area of the back. Moreover, FIGS. 5–6 and 8–9 indicate that in the preferred embodiment, apron 6 extends over a portion of the pelvis, further reducing the strain on the spine.

Natal support 2 is removed by detaching hooks 46 from looped areas 36 (if strap 8 has not already been removed.)

Then, hooks 34 of first and second flaps 30 and 32 are detached from loops 14 in similar fashion and apron 6 is removed from the back. Hooks 24 are then detached from loops 14 and support member 4 is removed from the human body.

Inasmuch as, in the preferred embodiment, support member 4, apron 6, strap 8, and belt 16 are manufactured out of a flexible fabric, each of these items can be easily washed or cleaned. Moreover, such flexible fabrics, whether elastic or inelastic in nature, will be relatively comfortable to wear for extended periods of time.

Since natal support 2, when properly installed, causes support body 9 to apply a compressive force to the lower abdomen, the forward-deflected spine is thereby urged rearward. In accordance with the objectives of the present invention, the restoration of the natural alignment of the spine tends to reduce muscle fatigue and stretching, and thereby reduce the pain inherent in pregnancy.

Accordingly, the improved natal support is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness, and understanding; but no unnecessary limitations are to be implied therefrom beyond the requirement of the prior art, because such terms are used for descriptive purposes and are intended to be broadly construed.

Moreover, the description and illustration of the invention is by way of example, and the scope of the invention is not limited to the exact details shown or described.

Having now described the features, discoveries, and principles of the invention, the manner in which the natal support is constructed and used, the characteristics of the construction, and the advantageous new and useful results obtained; the new and useful structures, devices, elements, arrangements, parts, and combinations are set forth in the appended claims.

Having thus described the invention, it is claimed:

1. A natal support for providing support to the body of a pregnant woman, said natal support comprising:
   a support member;
   an apron having a first flap and a second flap; said apron being adapted to rest at least partially adjacent the rear pelvic region;
   said first and second flaps being selectively attached to said support member;
   a strap having a first end and a second end; and
   said first and second ends being removably attached to said apron.

2. The natal support as set forth in claim 1 in which said support member further includes a belt, said belt having one end fixedly attached to said support member.

3. The natal support as set forth in claim 2 in which said belt further includes a terminal end removably attached to said support member.

4. The natal support as set forth in claim 3 in which said terminal end of said belt is removably attached to said support member with hook-and-loop fasteners.

5. The natal support as set forth in claim 1 in which said first and second ends of said strap are removably attached to said apron with hook-and-loop fasteners.

6. The natal support as set forth in claim 1 in which said first and second flaps of said apron selectively attach to said support member with hook-and-loop fasteners.

7. The natal support as set forth in claim 1 in which said support member is adapted to rest at least partially adjacent the front abdominal region.

8. The natal support as set forth in claim 1 in which said apron includes a plurality of panels connected together with hinge members.

9. A method for installing a natal support on the body of a pregnant woman comprising the steps of:
   installing a support member on the lower abdomen;
   placing an apron on the lower back;
   connecting a first detachable end and a second detachable end of a strap to the apron; and
   attaching said apron to said support member.

10. The method as set forth in claim 9 wherein said installing step further comprises the steps of positioning said support member over the abdomen, encircling the body with a belt, and affixing a terminal end of said belt to the support member.

11. The method as set forth in claim 9, further comprising the step of detaching the first and second detachable ends of the strap from the apron and removing the strap.

12. A natal support for providing support to the body of a pregnant woman, said natal support comprising:
   a support member;
   an apron selectively attached to said support; and
   a strap removably attached to said apron.

13. The natal support as set forth in claim 12 in which said support member includes a support body and a belt having first and second ends.

14. The natal support as set forth in claim 13 in which said first end is fixedly attached to said support body and said second end is removably attached to said support body.

15. The natal support as set forth in claim 12 in which said apron includes a plurality of panels connected by hinge members.

\* \* \* \* \*